United States Patent [19]
Joulain et al.

[11] Patent Number: 5,908,770
[45] Date of Patent: Jun. 1, 1999

[54] PROCESS FOR PREPARING BUTANONE DERIVATIVES

[75] Inventors: Daniel Joulain, Grasse, France; Claudio Fuganti, Milan, Italy

[73] Assignee: Robertet S.A., Grasse Cedex, France

[21] Appl. No.: 08/860,859

[22] PCT Filed: Jan. 11, 1996

[86] PCT No.: PCT/FR96/00045

§ 371 Date: Jul. 14, 1997

§ 102(e) Date: Jul. 14, 1997

[87] PCT Pub. No.: WO96/21739

PCT Pub. Date: Jul. 18, 1996

[30] Foreign Application Priority Data

Jan. 12, 1995 [FR] France ................................. 95.00472

[51] Int. Cl.⁶ ............................. C12P 7/26; C12N 9/02; C12N 1/14; C07C 45/00
[52] U.S. Cl. ...................... 435/148; 435/189; 435/255.1; 568/309
[58] Field of Search ................... 435/148, 189, 435/254.1, 255.1, 255.2, 255.6; 424/195.1; 514/678; 568/308, 309

[56] References Cited

U.S. PATENT DOCUMENTS 4,908,481  3/1990  Hoffmann et al. ...................... 568/308

FOREIGN PATENT DOCUMENTS 0 186 365  7/1986  European Pat. Off. .

OTHER PUBLICATIONS

Top et al. "Microbial resolution of organometallic planar chirality. Enantioselective reduction of orthe–and meta–substituted tricarbonylchromium benzaldehydes by baker's yeast," J. Organomet. Chem. (1991) 413: 125–135.

Sakai et al. "Asymmetric reduction of carbon–carbon double bonds of conjugated enones with fermenting baker's yeast," Bull. Chem. Soc. Jpn. (1991) 64: 3473–5.

Mochizuki et al. "Biochemical reduction of 3–oxoalkanoic esters by a bottom–fermentation yeast, Saccharaomyces cerevisiae IFO 0565," Biosci. Biotech. Biochem. 58(9): 1666–70, 1991.

Fogliato et al. "Baker's yeast reduction of arylidenecycloalkanones," Tetrahedron (1995) 51(37): 10231–240.

Servi, S. "Baker's yeast as a reagent in organic synthesis," Synthesis (1990) vol. 1, pp. 1–25.

Clark, G. "Para–hydroxy phenyl butane," Perfumer & Flavorist (1992) 17(4–7), Aug. 1992.

Fuganti et al. "Synthesis of (S)–O–benzylacetoin by yeast reduction of alpha–methelbenzlidenacetone," J. Chem. Res. (1985) Issue 1 pp. 21–22.

Klinman, J. "The mechanism of enzyme–catalyzed reduced nicotinamide adenine dinucleotide–dependent reductions," J. Biol. Chem. (1972) 247(24): 7977–87.

Takeshita et al. "Reduction of enones with baker's yeast," Tohoku Yakka Daigaku Kenkyu Nempo (Annu. Rep. Tohoku Coll. Pharm.) (1993) 40: 241–5.

Agricultural and Biological Chemistry, vol. 48, No. 6, Jun. 1984, Tokyo, pp. 1509–1516, Hirmoachi Ohta et al.

Primary Examiner—Jon P. Weber
Assistant Examiner—Susan Hanley
Attorney, Agent, or Firm—Browdy and Neimark

[57] ABSTRACT

A process for the preparation of a saturated butanone having a terminal substituted aryl group (I) by the selective reduction of an aryl-substituted $\alpha,\beta$-unsaturated butanone (II) is presented. The aryl moiety can be mono- or polysubstituted by one or more $C_1$–$C_6$ alkoxy, methylenedioxy or hydroxyl radicals and R is a $C_1$–$C_6$ radical. The $\alpha,\beta$-unsaturated butanone (II) is subjected to the action of the enzymes of a yeast or of a filamentous fungus to give a mixture of (I) and an alcohol (III). (I) and (III) are isolated and purified. (III) can be enzymatically oxidized to provide (I).

19 Claims, No Drawings

PROCESS FOR PREPARING BUTANONE DERIVATIVES

The present invention relates to an enzymatic process for preparing aromatic derivatives of butanone.

There is a confirmed general interest in producing rare natural products under physiological conditions, and in particular those which have intense organoleptic properties. These processes are all the more attractive when they can be carried out starting from easily available natural precursors. As products obtained in this way are considered natural, they can be used as ingredients for natural flavourings, which are preferred by consumers.

This category of substances includes arylated derivatives of butanone and in particular derivatives of phenylbutanone such as "raspberry ketone", "zingerone" and "Cassione®" (registered trade mark of the company Firmenich).

Raspberry ketone or 4-(4-hydroxyphenyl)-butan-2-one, was described for the first time as a characteristic component of raspberry flavour by H. Schinz and C. F. Seidel, Helv. Chim. Acta, 1957, 40, 1839. However, this substance was already known in its natural state as a component, among others, of a polygonacaea: Rheum palmatum, both in the form of an aglycone and in the form of glucosides (T. Murakami et al., Tetrahedron Letters, 1972, 2965; Y. Kashiwada et al., Chem. Pharm. Bull., 1986, 34, 3237). A gally-glucoside of raspberry ketone was also identified in a crassulacaea: Aeonium lindleyi (A. G. Gonzalez et al., Phytochemistry, 1976, 15, 344). According to a recent study, the glucoside of raspberry ketone accompanies the aglycone in the raspberry (A. Pabst et al., Phytochemistry, 1990, 29, 3853).

"Cassione®", or 4-(3,4-methylenedioxyphenyl)-butan-2-one, had not been found in nature until recently. For this reason, outside perfumery, its use had only been authorised in artificial food flavourings. Its presence was recently established in the essential oil of the aerial part of the rue plant: Ruta angustifolia Pers., a plant which is self-sown and grows in Malaysia (D. Joulain et al., Journal of Essential Oil Research, 1991, 3, 355), and it is therefore possible to now use this substance in food flavourings labelled "natural".

Zingerone is a component of ginger and of raspberry flavouring, but its contribution to this flavour is clearly less significant than that of raspberry ketone. The proportion of raspberry ketone in the raspberry is thus only between 9 and 174 µg per kilogram of fresh fruit, depending on to the variety (W. Borejsza-Wysocki et al., J.agric. Food Chem., 1992, 40, 1176).

The aromatic value of raspberry ketone is expressed by its olfactory detection threshold in water, comprised between 1 and 10 parts per billion (M. Larsen et al., Z. Lebensm. Unters. Forsch. 1990, 191, 129).

It will therefore be understood that raspberry ketone is an absolutely necessary substance, although insufficient to create a reconstituted raspberry flavouring.

Raspberry ketone is easily available on the market as a synthetic product at a very moderate cost, and it is therefore regularly used in flavouring compounds which are identical to nature or artificial.

However, there is no practical source of isolated natural raspberry ketone, which is vital to reconstitute a totally natural raspberry flavouring. The concentrations in which this substance exists in the raspberry fruit are indeed so low, even in the best of cases, that any attempt to extract it in order to isolate the substance would not be economically viable. A similar situation, although to a lesser extent, applies to Cassione®, owing to the small quantity present in essential oil of ruta and the great difficulty in isolating it with sufficient purity.

Attempts to produce raspberry ketone by fermentation de novo using certain strains of Nidularia have only allowed production of concentrations of raspberry ketone of the same order of magnitude as those observed in the fruit (P. Tiefel and R. G. Berger in Progress in Flavour Precursor Studies, P. Schreier and P. Winterhalter, publishers, Allured Publishing Co., Carol Stream, III, 1993, P 439–450). When these same authors add a supposed precursor of raspberry ketone such as paracoumaric acid to the culture medium, they do observe an increase in the concentration of raspberry ketone, but at a level which still remains excessively low. The complexity of the bioconversion mixture and the long incubation periods required are also unfavourable elements. Finally, the toxicity vis-à-vis the micro-organism of the various phenolic substances considered as possible precursors of raspberry ketone (and raspberry ketone itself) constitutes a severe problem in lifting the inhibition. Consequently, all these elements indicate that such a process is unsuitable for the production of raspberry ketone on a preparatory scale.

It would therefore be desirable to have an efficient and cost-effective preparation process, as natural as possible, for derivatives of arylbutanone type.

Now the Applicant has now discovered a preparation process for a butanone derivative of formula (I)

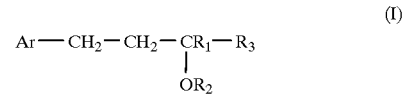

in which Ar represents an aryl group optionally mono- or polysubstituted by preferably $C_1$–$C_6$ alkyl, $C_1$–$C_6$ alkoxy, methylenedioxy or hydroxyl radicals, $R_1$ represents a hydrogen atom or represents together with $R_2$ a carbon-oxygen bond, $R_2$ represents a hydrogen atom or $R_2$ and $R_1$ together represent a carbon-oxygen bond, and $R_3$ represents a $C_1$–$C_6$ alkyl, preferably a methyl radical, characterised in that a compound of formula (II)

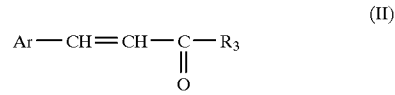

in which Ar and $R_3$ have the meaning already indicated, is subjected to the action of the enzymes of a yeast or of a filamentous fungus in order to obtain a mixture of compounds of formula I in which Ar, $R_1$, $R_2$ and $R_3$ have the meaning already indicated, which are isolated and separated if desired.

It is now well known that the reduction of an α,β-ethylenic carbonylated derivative by baking yeast proceeds by total reduction of the ethylenic function, leading essentially to a saturated alcohol. Fogliato et al. (Tetrahedron 1995, 51(37), page 10231) showed that the reduction of α-arylidenecyclanones by the same yeast proceeds by the action of different enzymes to lead to a mixture of saturated carbonylated derivative and of allylic (S)-carbinol resulting from the reduction of only the carbonyl group, the proportion of which varies from 35 to 50%. According to the present Application, α-arylideneketones of formula (II) behave, unpredictably, in a very different way. In fact, when they are subjected to the action of different micro-organisms according to the invention, including even baking yeast, the predominant formation of saturated ketone is observed, accompanied only by very minor quantities of saturated carbinol, and especially the total absence of allylic (S)-carbinol.

In formula (I) and in what follows, by "aryl group" is meant a group derived from a ring by substitution of a hydrogen atom, said ring containing from 6 to 10 carbon atoms and optionally comprising one or more heteroatoms, preferably oxygen, such as a phenyl or naphtyl radical. When the aryl group comprises one or more heteroatoms, it preferably comprises two and more particularly a single heteroatom. The said aryl group is preferably at least mono-substituted. It preferably comprises no more than four substitutions, and notably no more than two substitutions. Preferred substituents which can be mentioned are for example methyl, methoxy, ethoxy, methylenedioxy or hydroxyl radicals.

In what follows, yeasts and filamentous fungi are collectively designated "micro-organisms".

Among the micro-organisms which can be used according to the invention, there are particularly preferred as yeasts the Saccharomyces genus, in particular the *delbueckii* species (CBS 1146) and most particularly the *cerevisiae* species; there are also preferred the Hansenula genus, and in particular the *anomala* species (CBS 110), and the Debariomices genus, in particular the *hansenii* species (CBS 116). As filamentous fungi there are preferred those of the Pichia genus, in particular the *ohmeris* (CBS 5367), *stipitis* (CBS 5773) and most particularly *etchellsii* (CBS 2011) species.

The action of enzymes in baking yeast can be implemented according to several processes. In a particularly preferred process, micro-organisms in fermentation are used.

In fact, such an implementation allows the preparation of the expected products with an excellent yield and at a very low cost for the products used.

Advantageous fermentation conditions in the case of baking yeast (*Saccharomyces cerevisiae*) are for example as follows: 1 part by weight of glucose (or an equivalent quantity of sucrose or sugar beet treacle, etc.) is added to an agitated suspension of 10 parts by weight of moist baking yeast, or the equivalent quantity of yeast marketed in dehydrated form in 50 parts by weight of running water, at a temperature of 30 to 35°. When fermentation has started, the precursor is rapidly introduced (approximately 0.1 part), and the agitation is continued (while allowing the temperature to return to ambient temperature) for several days, for example 5 days. The reaction medium in which the biomass is predominant is then treated conventionally to extract the desired reaction products.

For this reason the subject of the present Application is in particular a preparation process for a butanone derivative as defined above, characterised in that a yeast or a filamentous fungus in fermentation is used, in particular in the exponential growth phase. A good selective reduction of the ketone of formula II is obtained, thus allowing the operation to be carried out with a low biomass/substrate ratio, which facilitates the extraction and purification of the expected product of formula I.

For example, when 4(4-hydroxy-phenyl)-but-3-en-2-one is added at the rate of 1 gram per liter of medium to a culture of the filamentous fungus Mucor subtilissimus (CBS 735.70) at its growth stage, its total disappearance is observed after 18 hours. After 14 hours of incubation, the proportion of expected product (raspberry ketone) is already 87.9%. When the duration of incubation is increased to 24 hours and beyond, the proportion of raspberry ketone decreases rapidly in favour of the compounds of formula I in which $R_1$ and $R_2$ represent hydrogen. Various yeasts lead to similar results.

For example, under similar culture and incubation conditions, *Pichia ohmeris* (CBS 5367) and *Pichia stipitis* (CBS 5773) both convert 70% of the buten-2-one precursor of formula II into raspberry ketone of formula I over 24 hours; after 48 hours, these yeasts only leave 13% and 18% of precursor unchanged respectively, without the formation of the compounds of formula I in which $R_1$ and $R_2$ represent hydrogen. The same applies to the yeasts *Hansenula anomala* (CBS 110), *Saccharomyces delbueckii* (CBS 1146) and *Debariomices hansenii* (CBS 116) although these produce a compound of formula I in which $R_1$ and $R_2$ represent hydrogen in minor proportions. Comparative performances after 48 hours of incubation for all five yeasts are shown in Table I.

| YEAST | % OF RASPBERRY KETONE OF FORMULA (I) |
|---|---|
| Pichia ohmeris | 87 |
| Pichia stipitis | 82 |
| Hansenula anomala | 82 |
| Saccharomyces delbueckii | 85 |
| Debariomices hansenii | 90 |

Under other conditions of implementation of the process according to the invention, a concentrate of yeast or filamentous fungus enzymes is used. Such a concentrate is for example the baking yeast concentrate marketed by the company SIGMA under reference Y-2875.

For this reason, a subject of the present Application is also a preparation process for a butanone derivative as defined above, characterised in that a concentrate of yeast enzymes or filamentous fungus is used.

Under other implementation conditions for the process described above, a protein extract is used as a concentrate of yeast enzymes or filamentous fungus. Such an extract is for example for baking yeast that marketed by the company SIGMA under the name "enzyme Sigma type 2".

For this reason, a subject of the present Application is also relates to a preparation process for a butanone derivative as defined above, characterised in that the above concentrate of enzymes is a proteinic extract of yeast.

In the case of utilisation of a concentrate of enzymes or of an extract, β-nicotinamide adenine dinucleotide is also advantageously used in its reduced form, or the corresponding phosphate (NADH and NADPH respectively). Such products are marketed in particular by the company SIGMA.

In the case of implementation of the above process under fermentation conditions, at the end of the incubation period deemed necessary and sufficient to isolate and purify the expected product of formula I, the pH of the medium is adjusted to 4–5, for example by the addition of citric acid, and an extraction is simply carried out using a solvent which is non-miscible with water, such as dichloromethane, tert-butyl ether, butanol, ethyl acetate or combinations of these solvents with less polar solvents such as cyclohexane. After evaporation of the extraction solvent, the residue is treated in order to crystallise the product of formula I such as raspberry ketone, for example using ethyl acetate/hexane or ethanol/water mixtures. A pure product is then obtained such as pure raspberry ketone in the form of white crystals with a melting point of 80–81° C.

During implementation of the process according to the invention, derivatives of formula (I) are preferably used in which Ar represents a phenyl radical, optionally substituted.

For this reason, a subject of the present Application is also a preparation process for a butanone derivative as defined above, characterised in that Ar represents a phenyl radical, optionally substituted.

When the phenyl radical is substituted, the substituents are advantageously situated in meta and/or para position of the derived chain of the butanone; the said substituents are more particularly chosen from the groups described above and in particular the methoxy, ethoxy, methylenedioxy and hydroxyl radicals.

For this reason, a more particular subject of the present Application is a preparation process for a butanone derivative as defined above, characterised in that the phenyl radical is substituted by at least one group chosen from the methoxy, ethoxy, methylenedioxy and hydroxyl groups.

Under absolutely preferential implementation conditions, a subject of the invention is a preparation process for a butanone derivative as defined above, characterised in that 4-(4-hydroxy-phenyl)-butan-2-one, 4-(3,4-methylenedioxyphenyl)-butan-2-one or 4-(4-hydroxy-3-methoxyphenyl)-butan-2-one is prepared.

A more particular subject of the invention is also a preparation process as defined above, characterised in that, in formula (I), $R_1$ together with $R_2$ represent a carbon-oxygen bond.

A preferred family of products prepared by the process according to the invention corresponds to the formula

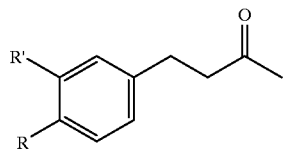

in which R and R' have the meanings already indicated for substituents of the aryl group.

In the implementation of the above process, a mixture of the products of formula (I) is obtained in which the ketonic derivatives are accompanied by minor quantities of the corresponding saturated alcohol.

According to the chromatographic analyses carried out during the course of the reaction, it is observed that the ethylenic double bond is first reduced, followed by the ketone function. This preferential reduction of a double bond situated both in α position of a carbonyl group and conjugated with an aromatic ring is quite unexpected and had never been described before.

In the particular case of the preparation of raspberry ketone, corresponding to a derivative of formula (I) in which Ar represents a phenyl radical substituted by a hydroxyl in position 4, it is observed that the secondary alcohol formed by bioreduction of the ketone function is of over 85% S configuration as is indicated by analysis of the crude product after acetylation, by high pressure liquid chromatography (HPLC) using a chiral column (for example, of the Chiralcel-OD type marketed by the company Daicel). For this reason and according to prior knowledge in the field of biochemistry, this secondary alcohol can be reoxidated into raspberry ketone if desired, via an alcoholdehydrogenase such as for example that extracted from a horse's liver, for example in the presence of an excess of acetaldehyde as hydrogen acceptor.

It is also possible to carry out the bioreduction otherwise than with whole micro-organism cells, in particular of yeast by using for example a protein extract of this micro-organism. In this case, if a stoichiometric quantity of cofactor is not used, it is advantageous to use a system which recycles it (up to thirty times), using the dehydrogenase formate. Such an enzyme system is preferably implemented in an immobilized form. Standard processes of the prior art in particular have recourse to polyethyleneglycols with a molecular weight in the region of 10,000 and to membranes allowing molecules of appropriate size to pass through.

The starting products of formula (II) are known products. In particular, 4-(4-hydroxyphenyl)-but-3-en-2-one forming the reduction substrate for natural raspberry ketone can be easily obtained, without any quantitative limits, by heated contact between 4-hydroxybenzaldehyde and an excess of acetone in an aqueous solution the pH of which has been adjusted to a value allowing the 4-hydroxybenzaldehyde to pass into solution. These two elements are themselves available as natural substances. The acetone is thus obtained by fermenting glucose in particular using *Clostridium acetobutylicum*. For its part, 4-hydroxy-benzaldehyde can for example be released by simple heating in the presence of emulsin of a suspension of aqueous dhurrin, a glucoside similar to amygdalin which exists in young sorghum shoots (*Sorghum vulgare*). A subsequent extraction using a solvent and a washing to eliminate the hydrocyanic acid also released in this operation are standard in such cases.

4-hydroxybenzaldehyde can also be obtained by biodegradation of piceide, a stibene present in the bark of the spruce tree, according to Y. Shiotsu et al., Makuzai, 1989, 35, page 826.

It can be seen that a significant number of the derivatives of formula (I) can be prepared under physiological conditions from natural products or originating from natural products.

Finally, the invention relates to a preparation process for a butanone derivative as defined above, characterised in that in addition, a usual enzymatic oxidation is carried out on a compound of formula (I) in which $R_1$ and $R_2$ represent a hydrogen atom, to obtain the corresponding compound of formula (I) in which $R_1$ together with $R_2$ represent a carbon-oxygen bond.

The following examples illustrate the present invention.

EXAMPLE 1

Microbiological preparation of 4-(4-hydroxyphenyl)-butan-2-one and of 4-(4-hydroxyphenyl)-butan-2-ol.

2.5 liters of water then 100 grams of D-glucose are placed successively in a receptacle in the open air, equipped with an agitation system. While being agitated, this solution is then heated to a temperature of approximately 30° C., then 1 kg of ordinary baking yeast in its moist commercial form is added in one lot. The suspension is vigorously agitated at a temperature of 30° C. to 35° C., after a few minutes the start of fermentation is observed, visible by the formation of a foam due to the production of carbon dioxide. A concomitant increase in temperature of 2 to 5° C. is also observed. With the temperature now close to 35° C., a solution of 8.1 grams of 4-(4-hydroxyphenyl)-but-3-en-2-one (0.050 mole) in 20 ml of ethanol at 96° C. is then added dropwise over 10 minutes. While agitation is maintained, the mixture is allowed to return to ambient temperature, and these conditions are maintained for 48 hours.

The incubation medium is then subjected to a continuous liquid-liquid extraction for 12 hours using methyl tert-butyl ether (MTBE). After elimination of the solvent by evaporation, approximately 10 grams of a solid crude product is obtained, mainly constituted, according to analysis by gas chromatography combined with a mass spectrometer by:

56% of 4-(4-hydroxyphenyl)-butan-2-one

37% of 4-(4-hydroxyphenyl)-butan-2-ol

3% of unchanged initial substrate.

The product is then purified as follows: the crude product is heated to a temperature of approximately 60° C. with the minimum amount of ethyl acetate, then hexane is added dropwise to this clear dark yellow solution until signs of turbidity are observed. This solution is left at ambient temperature. A crystallised product separates out. This is separated and 4.8 g of 4-(4-hydroxyphenyl)-butan-2-one is obtained which is more than 99% pure. Recrystallisation from a mixture of water and methanol provides a product of analytic quality with a melting point of 84° C.

EXAMPLE 2

Enzymatic preparation of 4-(4-hydroxyphenyl)-butan-2-one and of 4-(4-hydroxyphenyl)-butan-2-ol.

20 mg of 4-(4-hydroxyphenyl)-but-3-en-2-one and 70 mg of β-nicotinamide adenine dinucleotide in reduced form (NADH), a product marketed by the company Sigma under reference N-8129 is added to a solution of 100 mg of protein extract of yeast, such as that marketed by the company Sigma under reference Y-2875 in 10 ml of phosphate buffer (pH 7), and maintained under agitation at a temperature of 20°.

Agitation is carried out for 24 hours at this temperature, then the reaction mixture is analysed by thin-layer chromatography, while observing the appearance of the expected product. After 75 hours, the reaction mixture is extracted with three times 2 ml of ethyl acetate. Analysis of the crude reaction product by gas chromatography combined with a mass spectrometer indicates that the mass is essentially constituted by initial substrate, by raspberry ketone and by 4-hydroxybenzaldehyde in proportions of 100/5/0.6.

EXAMPLE 3

Enzymatic preparation of 4-(4-hydroxyphenyl)-butan-2-one and of 4-(4-hydroxyphenyl)-butan-2-ol.

10 mg of 4-(4-hydroxyphenyl)-but-3-en-2-one is added to a solution of 50 mg of Sigma type 2 enzyme extract and 35 mg of β-nicotinamide adenine dinucleotide phosphate in reduced form (NADPH), marketed by the company Sigma under reference N-1630, in 5 ml of phosphate buffer 0.1 M (pH 7) at a temperature of 25° C. After agitation at this temperature for 6 hours, the observed conversion rate is 14%. 25 mg of additional enzymatic extract is then added. Analytical monitoring of the progress of bioconversion indicates that the conversion rate reaches a maximum of 30% after approximately 20 hours.

EXAMPLE 4

Enzymatic preparation of 4-(4-hydroxyphenyl)-butan-2-one from 4-(4-hydroxyphenyl)-butan-2-ol.

1 mg of NAD+, 2 mg of HLADH (horse liver alcohol dehydrogenase), 60 microliters of acetaldehyde and 8.3 mg of 4-(4-hydroxyphenyl)-butan-2-ol in the form of an S enantiomeric excess of 64% are successively added at an ambient temperature of 20° C. to a solution of 0.050 M of agitated 3-(N-morpholino)propanesulphonic acid (pH 7). After 40 hours of agitation at this temperature, the reaction medium is extracted, it is analysed by chromatography as previously and the presence of 4-(4-hydroxyphenyl)-butan-2-one and of 4-(4-hydroxyphenyl)-butan-2-ol is observed which are isolated. After acetylation, analysis of this alcohol by chirospecific liquid chromatography indicates that is principally R enantiomer, with an enantiomeric excess of 84%.

EXAMPLE 5

Microbiological preparation of 4-(4-hydroxyphenyl)-butan-2-one.

A culture is prepared of *Mucro subtilissimus* (CBS 735.70), deposited on Dec. 22, 1995 at the Collection Nationale de Cultures de Microorganismes of the Institut Pasteur in Paris under number I-1653, on a solid medium (malt: 20 g/l, peptone: 5 g/l, glucose: 20 g/l, agar: 15 g/l), at a temperature of 24° C. for 4 days. This culture is used to inoculate a 300 ml flask containing 50 ml of a culture medium constituted by malt: 20 g/l, peptone: 5 g/l, glucose: 20 g/l, at a rate of approximately 5 ml per 50 ml of medium. After 24 hours of agitation at a temperature of 24° C. and a rate of 140 shaking movements per minute, this culture is itself used as an inoculum and introduced into a 6-liter fermentor containing the same medium, at a rate of 5% of the medium quantity. After the fungus has grown for 12 to 24 hours, 4-(4-hydroxyphenyl)-but-3-ene-2-one is added in the form of a solution in the minimum amount of ethanol at 96%, at a rate of 1 to 2 grams per liter of medium.

After 15 hours, the progress of the conversion is rapidly observed by analysis of a test sample, and an extraction is carried out after adding a sufficient quantity of citric acid to adjust the pH of the medium to 5. After the usual treatments, crystallised raspberry ketone or 4-(4-hydroxyphenyl)-butan-2-one is isolated as in Example 1, with a molar yield of 80%.

EXAMPLE 6

Microbiological preparation of 4-(4-hydroxyphenyl)-butan-2-one.

A process similar to that in Example 5 was implemented starting from the yeast *Pichia etchellsii* (CBS 2011), deposited at the Collection Nationale de Cultures de Microorganismes at the Institut Pasteur in Paris on Dec. 22, 1995 under number I-1652; the raspberry ketone is also obtained with an excellent yield.

We claim:

1. A process for preparing a butanone consisting of the formula (I):

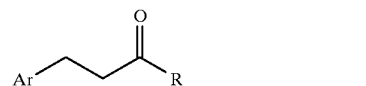

(I)

wherein Ar is an aryl group that is mono- or polysubstituted by one or more $C_1$–$C_6$ alkoxy, methylenedioxy or hydroxyl radicals and R is a $C_1$–$C_6$ radical, comprising:

(a) subjecting a compound of formula (II):

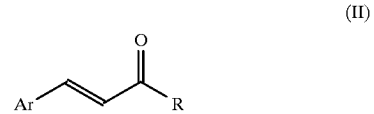

(II)

wherein Ar and R have the meanings already indicated, to the action of the enzymes of a yeast or of a filamentous fungus to give a mixture of (I) and an alcohol of formula (III):

(III)

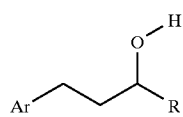

wherein Ar and R have the meanings already indicated; and (b) isolating and purifying said butanone (I).

2. The process of claim 1, wherein said enzymes are produced in situ.

3. The process of claim 1, wherein said enzymes are in the form of a concentrate.

4. The process of claim 3, wherein said concentrate is a protein extract.

5. The process of claim 1, wherein Ar is a substituted phenyl radical.

6. The process according to claim 5, wherein the phenyl radical is substituted by at least one member selected from the group consisting of methoxy, ethoxy, methylenedioxy and hydroxyl.

7. The process according to claim 1, wherein 4-(4-hydroxyphenyl)-butan-2-one is prepared.

8. The process according to claim 1, wherein 4-(4-hydroxy,3-methoxyphenyl)-butan-2-one is prepared.

9. A process for preparing a butanone consisting of the formula (I):

(I)

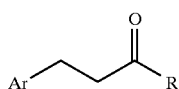

wherein Ar is an aryl group that is mono- or polysubstituted by one or more $C_1$–$C_6$ alkoxy, methylenedioxy or hydroxyl radicals and R is a $C_1$–$C_6$ radical, comprising:

(a) subjecting a compound of formula (II):

(II)

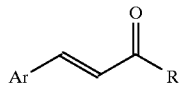

wherein Ar and R have the meanings already indicated, to the action of the enzymes of a yeast or of a filamentous fungus to give a mixture of (I) and an alcohol of formula (III):

(III)

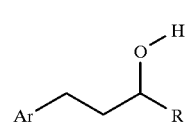

wherein Ar and R have the meanings already indicated;

(b) isolating and purifying said butanol (III);

(c) enzymatically oxidizing said purified alcohol (III) to the corresponding butanone of formula (I); and (d) isolating and purifying said butanone.

10. The process of claim 9, wherein said enzymes of step (a) are produced in situ.

11. The process according to claim 10 wherein Ar represents a substituted phenyl radical.

12. The process according to claim 11 wherein the phenyl radical is substituted by at least one member selected from the group consisting of methoxy, ethoxy, methylenedioxy and hydroxyl.

13. The process according to claim 10 wherein the compound prepared is selected from the group consisting of 4-(4-hydroxyphenyl)-butan-2-one and 4-(4-hydroxy,3-methoxyphenyl)-butan-2-one.

14. The process of claim 9, wherein said enzymes of step (a) are in the form of a concentrate.

15. The process of claim 14, wherein said concentrate is a protein extract.

16. The process according to claim 14 wherein the compound prepared is selected from the group consisting of 4-(4-hydroxyphenyl)-butan-2-one and 4-(4-hydroxy,3-methoxyphenyl)-butan-2-one.

17. The process according to claim 14 wherein Ar represents a substituted phenyl radical.

18. The process according to claim 17 wherein the phenyl radical is substituted by at least one member selected from the group consisting of methoxy, ethoxy, methylenedioxy and hydroxyl.

19. The process of claim 9, wherein Ar is a substituted phenyl radical.

* * * * *